(12) United States Patent
Anderson

(10) Patent No.: US 6,850,323 B2
(45) Date of Patent: Feb. 1, 2005

(54) LOCALLY ENHANCED RAMAN SPECTROSCOPY WITH AN ATOMIC FORCE MICROSCOPE

(75) Inventor: Mark S. Anderson, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 355 days.

(21) Appl. No.: 10/062,081

(22) Filed: Jan. 31, 2002

(65) Prior Publication Data

US 2002/0105641 A1 Aug. 8, 2002

Related U.S. Application Data

(60) Provisional application No. 60/266,693, filed on Feb. 5, 2001.

(51) Int. Cl.[7] .............................. G01J 3/44; G01J 3/30; G02B 21/00
(52) U.S. Cl. .................... 356/301; 356/318; 250/458.1; 250/459.1
(58) Field of Search ................................ 356/301, 317, 356/318, 73; 250/458.1, 459.1, 461.1, 461.2

(56) References Cited

U.S. PATENT DOCUMENTS

| 5,017,007 A | * | 5/1991 | Milne et al. ................. 356/301 |
| 5,479,024 A | * | 12/1995 | Hillner et al. ............ 250/458.1 |
| 6,002,471 A | | 12/1999 | Quake |
| 6,466,309 B1 | * | 10/2002 | Kossakovski et al. ......... 356/73 |
| 6,643,012 B2 | * | 11/2003 | Shen et al. .................. 356/301 |

OTHER PUBLICATIONS

Ayaras et al, Surface enhancement in near–filed Raman spectroscopy, Appl. Physics Letters, Jun. 2000, v. 76, pp 3911–3913.*

* cited by examiner

*Primary Examiner*—Layla G. Lauchman
(74) *Attorney, Agent, or Firm*—Daniel L. Dawes; Myers Dawes Andras & Sherman LLP

(57) ABSTRACT

An atomic force microscope (AFM) tip is used to selectively produce surface enhanced Raman scattering (SERS) for localized Raman spectroscopy. Spectra of thin films, undetectable with a Raman microprobe spectrometer alone, are readily acquired in contact with a suitably gold-coated AFM tip. Similarly, an AFM tip is used to remove sample layers at the nanometer scale and subsequently serve as a SERS substrate for ultra-trace analysis. This demonstrates the interface of an AFM with a Raman spectrometer that provides increases sensitivity, selectivity and spatial resolution over a conventional Raman microprobe. An AFM guiding the SERS effect has the potential for targeted single molecule spectroscopy.

14 Claims, 2 Drawing Sheets

LOCALLY ENHANCED RAMAN SPECTROSCOPY WITH AN ATOMIC FORCE MICROSCOPE

RELATED APPLICATIONS

The present application is related to and claims priority under 35 USC 120 to U.S. Provisional patent application Ser. No. 60/266,693, filed on Feb. 5, 2001, which is incorporated herein by reference.

BACKGROUND OF THE INVENTION

1. Field of the Invention

The invention relates to atomic force microscope (AFM) tip used to selectively produce surface enhanced Raman scattering (SERS) for localized Raman spectroscopy.

2. Description of the Prior Art

Atomic force microscopy (AFM) has seen rapid growth in a remarkably short time. There has been considerable effort to integrate chemical analysis into the AFM's ability to image at high spatial resolution with some of the most promising efforts combining optical spectroscopy with the AFM. Research groups working with near field scanning optical microscopy (NSOM) are moving in a number of different directions, namely into the field of optical absorption spectroscopy. Others are working to combine AFM and photothermal detection with infrared spectroscopy. However, these techniques require complicated interfaces or provide limited chemical information. An efficient AFM-spectrometer interface, analogous to a scanning electron microscope with energy dispersive spectroscopy, would have widespread application in materials, semiconductor and biological research. The ability of the AFM to remove surface layers can also be exploited to enhance the selectivity and spatial resolution of spectral and chemical measurements of surfaces.

BRIEF SUMMARY OF THE INVENTION

The invention is an apparatus for analyzing a sample comprising an atomic force microscope; and a Raman spectrometer working in combination or integrated into a single instrument. The Raman spectrometer is optically coupled to the atomic force microscope. The atomic force microscope has a atomic force microscope (AFM) tip with a coating disposed thereon to provide spatially selective enhancement of a Raman signal using a surface enhanced Raman scattering (SERS) effect. The Raman spectrometer has at least a quasi-monochromatic light source or a laser. The coating is comprised of particles having a size smaller than the shortest wavelength of incident light directed thereon from the light source so that the particles generate surface plasmons, which couple with the sample to produce the enhanced Raman signal.

In the illustrated embodiment the AFM tip is comprised of silicon and the coating is a metal or a semi-metal. However, the coating includes such embodiments as sputter-coated gold, silver or copper. However, it must be clearly understood that other metals or semi-metals may be used, or any substance capable of exhibiting a similar spatially selective enhancement of a Raman signal using a surface enhanced Raman scattering (SERS) effect, such as platinum, tungsten, indium, iridium and iron. In the illustrated embodiment the sputter-coated gold is Argon sputter coated with a mean grain size of no greater than about 45 nm. Clearly, other mean grain sizes, shapes and aspect ratios could also be employed.

The AFM tip generates an electromagnetic field enhancement near the tip by generation of surface plasmons in the coating in response to irradiation by an at least a quasi-monochromatic light source. In addition the coating of the AFM tip coordinates with molecules in the sample to form charge transfer states with energy levels in the coating to produce a chemical enhancement of the Raman signal.

In one embodiment the tip is placed directly on a surface of the sample for local surface enhanced Raman spectroscopy. In a second embodiment the tip is used to collect surface molecules from the sample and the Raman signal is produced from the collected surface molecules on the tip.

In the illustrated embodiment the spatially selective enhancement of the Raman signal is generated within a radius of about 15 μm or less.

In the preferred embodiment the light source illuminates the tip from a side direction approximately perpendicular to an imaginary line connecting the tip and the sample or where the sample has a generally planar surface in a direction approximately parallel to the sample. The light source is focused in the near field of the tip.

The apparatus in one embodiment may include means for oscillating the tip in a direction approximately perpendicular to the direction of incident light, such as a piezoelectric oscillator coupled to the tip.

In still another embodiment the coating is composed of discrete particles of metal or semi-metal to define enhanced particles.

The apparatus may be employed in a wide variety of applications, such as where the sample comprises a microdevice or MEMS device that has failed, a biological substance or an in situ sample in a remote sampling situation at an inaccessible geologic or interplanetary location.

In addition to the apparatus described above, the invention comprises a method of providing such a combination of apparatus, and a method for performing Raman spectroscopy with spatially selective enhancement of the Raman signal using a surface enhanced Raman scattering (SERS) effect between the tip and the sample.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
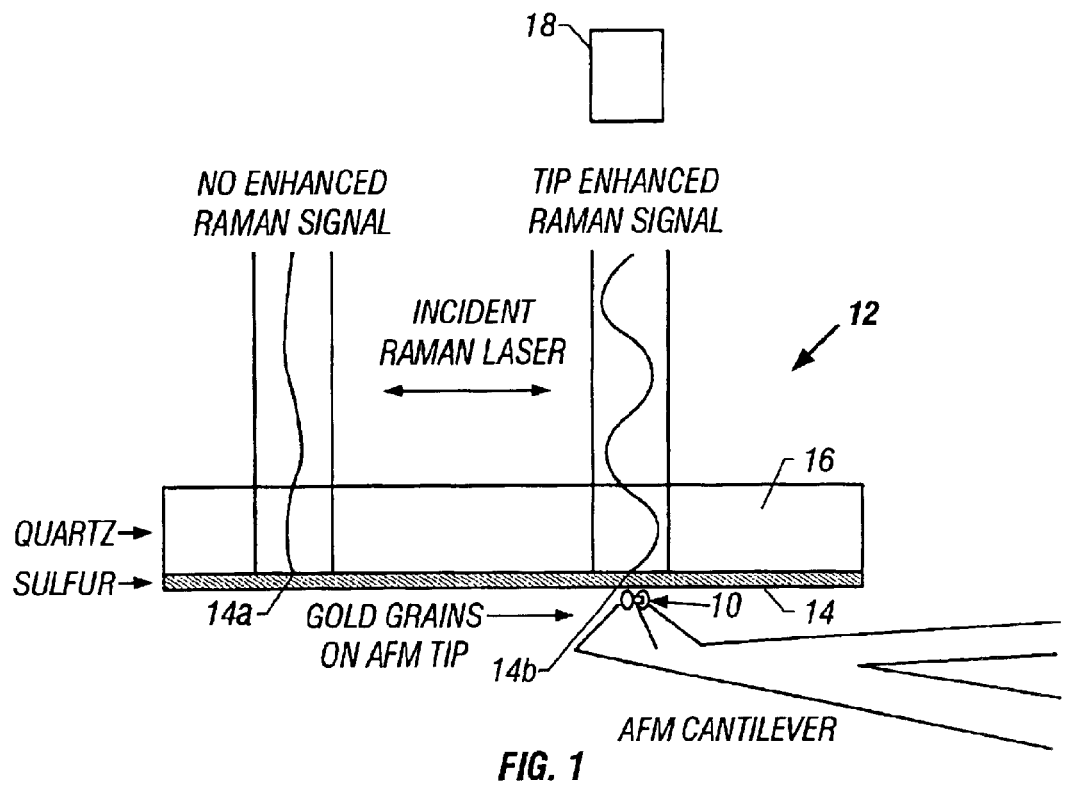
FIG. 1 is a simplified schematic of an AFM tip on a thin sulfur film deposited on quartz.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

An atomic force microscope (AFM) tip is used to selectively produce surface enhanced Raman scattering (SERS) for localized Raman spectroscopy. Spectra of thin films, normally undetectable with a Raman microprobe spectrometer alone, are readily acquired with the use of a suitably gold-coated AFM tip according to the invention. Alternatively, an AFM tip is used to remove sample layers at the nanometer scale and subsequently serves as a SERS substrate for ultra-trace analysis. The combination of an AFM with a Raman spectrometer thus provides increased sensitivity, selectivity and spatial resolution over a conventional Raman microprobe. An AFM guiding the SERS effect has the potential for even targeted single molecule spectroscopy.

When a conventional AFM tip 10 depicted in FIG. 1, which tip 10 is suitably coated with gold, can provide spatially selective enhancement of a Raman signal from a sample using a surface enhanced Raman scattering (hereinafter SERS) effect. The SERS effect exploits a property of nanometer sized metal particles or surface grains on the AFM tip. Incident laser photons are absorbed into the metal particles on the tip through oscillations of surface electron charge density, which oscillations are defined as plasmons. This absorption effect can couple with molecules in close proximity to the tip and provide an efficient pathway to transfer energy to the molecular vibrational modes of the sample, and generate Raman photons, which are photons in a sample beam, which are inelastically scattered from the sample or hence suffer a change in wavelength. The Raman spectra of a molecule is a unique fingerprint by which the sample may be nondestructively identified. The enhancement is maximized when the metal grains of the tip are smaller than the incident laser wavelength and the metal of the tip has the optical properties to generate surface plasmons. The greatest enhancements are observed with silver, gold, and copper with grain diameters between 10 and 200 nm and laser light in the range of 0.2 $\mu$m to 25 $\mu$m.

In addition to an electromagnetic field enhancement, there is an additional chemical enhancement that results when a molecule coordinates with the metal particle surface and forms charge transfer states with the energy levels of the metal. This enhancement results in a charge transfer transition in the visible wavelength region and a surface localized resonance Raman enhancement. Recently, enhancement factors of $10^8$ to $10^{14}$ have been reported with single molecule detection of molecules absorbed on a silver substrate.

The challenge is to develop a method that readily incorporates Raman spectroscopy with an AFM, generally denoted by reference numeral 12 in FIG. 1, without using the elaborate detection schemes required for near field optical detection or expensive specialized tips. FIG. 1 is a simplified schematic of an AFM tip on a thin sulfur film 14 deposited on quartz slide 16. The illustrated embodiment uses a film 14 of sulfur as the analyte, but it must of course be understood that the analyte is entirely arbitrary and may include any substance which provides a Raman spectrographic signal. This arrangement allows the tip-localized SERS effect to be compared to the non-enhanced film 14a through the backside of the transparent quartz slide 16.

According to the invention a two-part strategy uses conventional AFM and Raman microprobe instruments. In the first approach, the gold-coated tip 10 is placed directly on a surface 14b for local surface enhanced Raman spectroscopy. While gold is recited at the coating of tip 10 of the illustrated embodiment, the invention may employ any AFM tip now known or later devised consistent with the teachings of the invention. A second approach uses an AFM tip 10 that has collected surface molecules from a sample 14. In this case, the tip 10 serves as the SERS substrate for enhancement of the collected, separated analyte.

Figure 2:
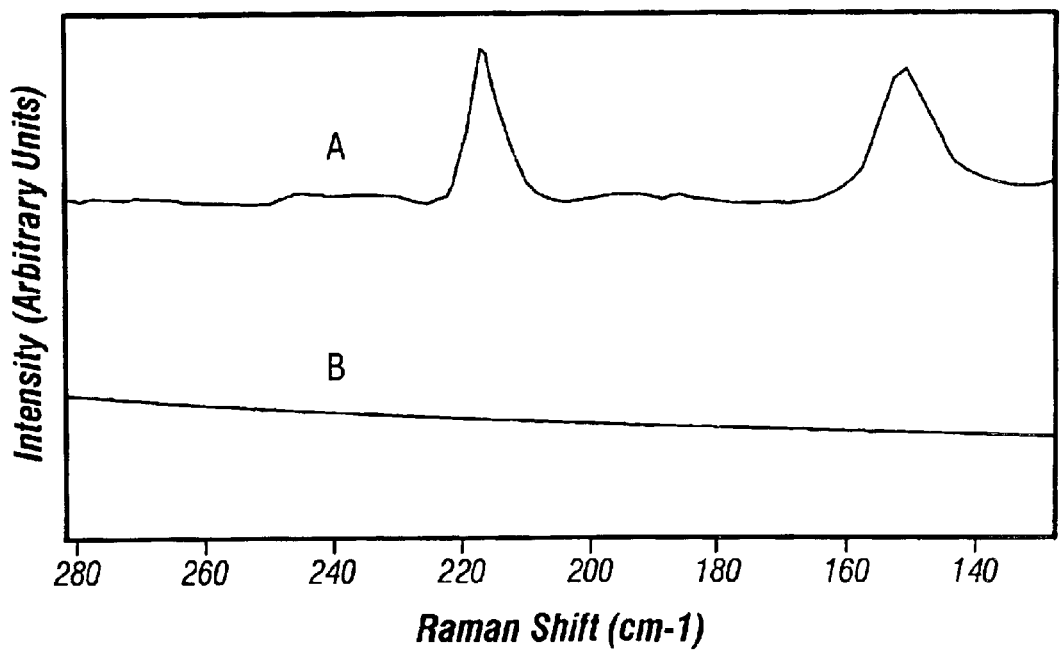
FIG. 2 is a graph of a Raman spectrum demonstrating gold-coated AFM tip causing a local surface enhanced Raman effect on a Sulfur film as shown by graph A. When the beam is focused away tip on the film the Raman signal is undetectable using the same microprobe parameters as shown by graph B.

The embodiments which illustrate the invention are relatively simple and direct. Conventional silicon AFM tips 10 were Argon-sputter coated with gold using a device found in many SEM laboratories. The silicon tips 10 (TESP) were from Digital Instruments (Santa Barbara, Calif.) and were coated with a Technics Hummer X Argon plasma coater for 120 seconds at 8 mA and 1200V in 100 mTorr Argon with a distance of 5 centimeters from the target. The sputtering produced a mean grain size of 45 nm as measured on a silicon reference coupon using an AFM 12. The AFM 12 used was a Digital Instruments Nanoscope III. The Raman instrument, symbolically denoted by reference numeral 18, was a Kaiser Holoprobe using a 785-nm laser excitation interfaced to an optical microscope. The embodiments used a 10X objective. The instrument or system 18 uses a CCD camera (Photometics Ltd.) and is equipped with a Kaiser holographic notch filter to suppress the Rayleigh scattering. Exposure times were 1 second with 10 accumulations co-added. To test the potential for a gold-coated AFM tip 10 to provide local surface enhancement, a quartz slide coated with a sulfur film 14 was examined. The sulfur was in a thin (~10 micron), uniform layer 14 deposited from an acetone solution. The thin sulfur film 14, without the tip, was undetectable with the above selected and optimized Raman microprobe instrument 18 parameters. The AFM tip-cantilever substrate or slide 16 was clipped to the coated side of the slide 16 with the AFM tip 10 in contact with the surface 14b. The slide 16 was placed in the Raman microscope 18 and the laser beam could be directed on the tip 10 or ~15–25 microns away to measure the local enhancement. A schematic of the configuration used is given in FIG. 1. This arrangement allows a direct comparison of Raman spectra from the local tip enhanced area 14b to areas 14a several microns away from the tip 10. The locally enhanced film 14b produced a high signal-to-noise ratio spectrum of sulfur when the tip-film interface 10–14 was in the Raman microprobe beam as shown in graph A of FIG. 2. When the microprobe beam was ~15 microns away from the tip 10, the sulfur film 14b was undetectable using the same instrument parameters as shown in graph B of FIG. 2. The enhancement factor was estimated to be $10^4$ or greater based on comparison to thicker films using the same parameters.

The enhancement factor can only be bounded because the area of the locally enhanced film 14b is not known. Side illumination of the AFM tip 10 also produced an enhanced signal. This is of practical importance for interfacing a Raman spectrometer 18 to an AFM 12. The laser probe beam can be focused from the side through fiber optics with a relatively simple interface (not shown). It is not necessary to use the tip 10 as the optical waveguide that requires a more complicated interface. The parameters that dominate the field enhancement are the dielectric constant and the radius of the tip 10. In the illustrated embodiment, Argon-sputtered gold produces grains approximately 45 nm mean diameter on the AFM tip apex. Using silver and controlling the grain size could maximize the SERS effect.

Figure 3:
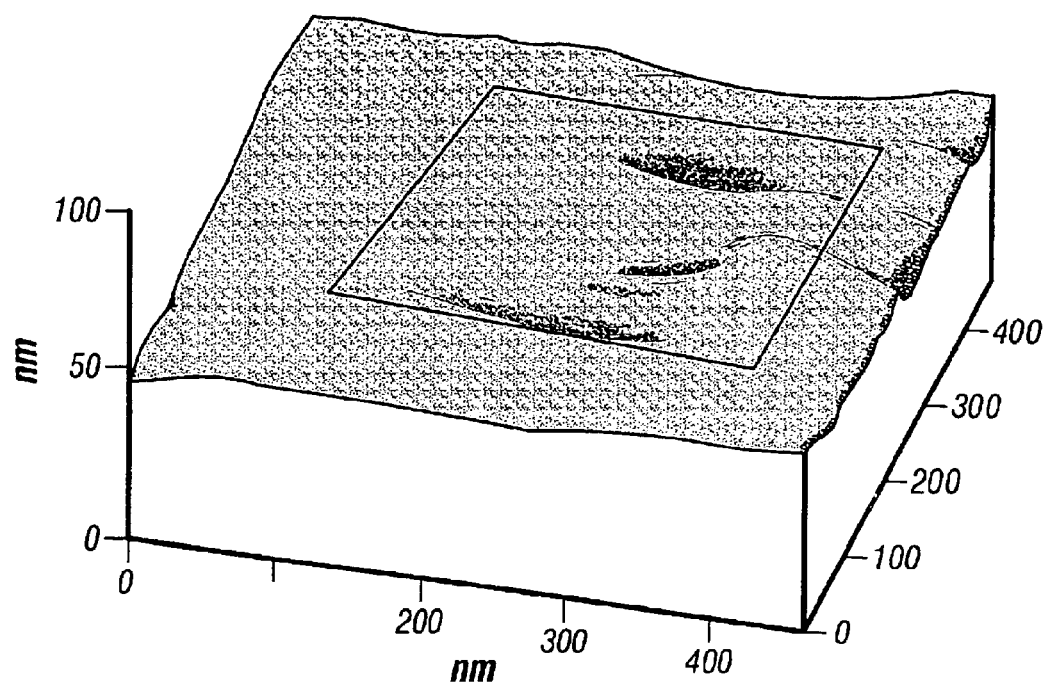
FIG. 3 is a three dimensional depiction of a C60 film sampled by an AFM tip, at high force, inside the marked 250×250 nm region.
Figure 4:
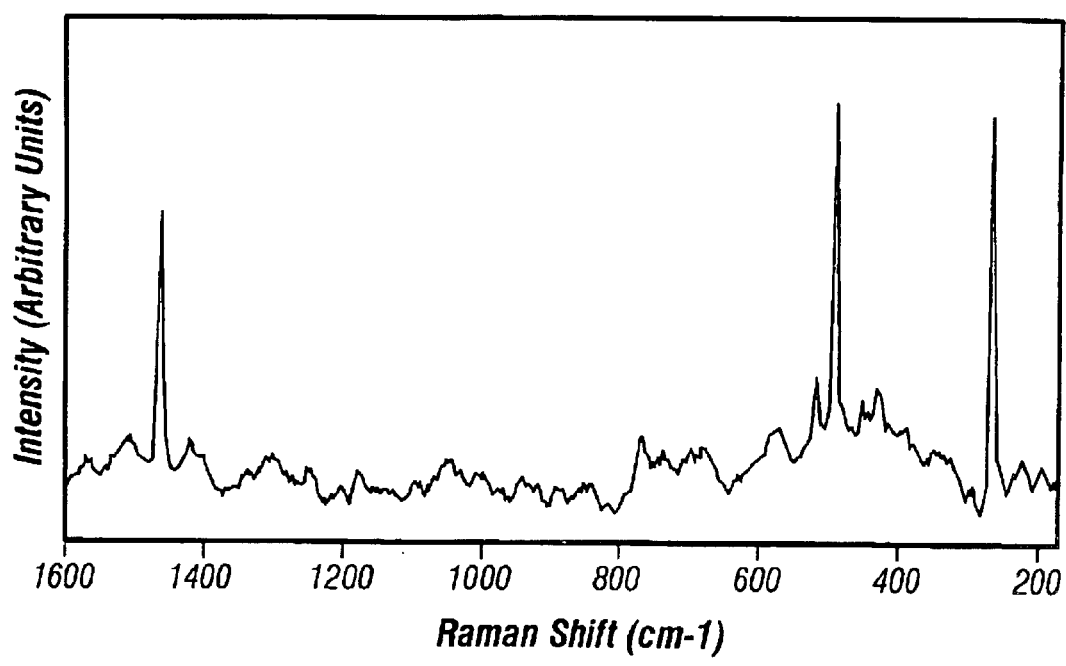
FIG. 4 is a three dimensional depiction of a gold-coated AFM tip was used to removed C60 layers from film surface.

In the second embodiment, surface material 14 was removed by an AFM 12 and collected on the gold-coated tip 10. The AFM cantilever-tip 10 was then placed in the Raman microscope 18 and used as a SERS substrate. The sample surfaces were first AFM scanned at high tip force, in contact mode, by adjusting the AFM cantilever set point. This caused the tip 10 to move and concentrate surface layers from film 14 at the edge of a scan region and to collect on the AFM tip 10. A similar procedure is detailed elsewhere for AFM sampling for infrared microscopy. See M. S. Anderson, Applied Spectroscopy, Vol. 54 Number 3, March 2000. This was tested with a C60 film solution 14 cast on a mica substrate 16. A 250×250-nm region was scanned at high AFM tip force then zoomed out and imaged at 500× 500-nm area at lower force. The amount of C60 collected from the surface 14 on the AFM tip 10 is estimated to be ~10 femtograms based on AFM image of the altered inner sampled region as shown in FIG. 3. The surface enhanced Raman spectrum of the C60 on the tip is given in the graph of FIG. 4. The tip 10 functions as SERS substrate 16 for ultra trace detection of the removed material. This embodiment was reproduced with a plasticized polyvinylchloride sample, where the tip 10 removed plasticizer for subsequent Raman spectroscopic analysis. This technique provides remarkable sensitivity and the samples were removed with a high degree of specificity.

The ultimate potential for improved spatial resolution and single molecule spectroscopy will now be considered. Lateral external illumination of a probe tip 10 with laser radiation can produce an intensity enhancement of $5 \times 10^5$ in the near field underneath the tip 10. This focusing of laser radiation in the near field of the tip 10 (FOLANT) technique has been applied to material processing down to 10 nanometer lateral dimensions. FOLANT has been used in apertureless optical spectroscopy, where vertical oscillation of a probe tip 10 modulated the optical signal and distinguished it from the unmodulated background interference. This technique has achieved 1 nm optical resolution. In the SERS technique used in the illustrated embodiment of the invention, background interference is less of a problem. This is because the signal is at a different frequency than the incident radiation and the chemical enhancement component is from molecular absorption. However, the tip modulation method could be useful in distinguishing field enhanced areas 14b from molecular absorption on the tip.

Others have reported SERS enhancements on discrete silver particles of $10^{14}$–$10^{15}$ and a SERS spectra on ~300 molecules has been reported using NSOM on a two-dimensional substrate coated with silver islands. These results are much larger than what is reported from measurements using conventional SERS, which are population-averaged results over a large ensemble of particles, where the particles are assumed to be contributing equally to the enhanced signal. The intrinsic enhancement of individual particle can be $10^6$–$10^7$ higher than the ensemble averaged particle, because only a fraction of the particles have the size and shape for very large enhancements. The invention thus has the potential of using AFM-SERS to target single molecules. The tip 10 must have the properties of these so called "hot" particles and therefore a rapid method of screening the suitable tips would be useful. An AFM cantilever array could be used so many tips could be evaluated rapidly. It should be noted that ~50% of the tips used during the course of this study did produce useful enhancement and 5% produced large enhancements. Of course, there are applications that do not require such extreme sensitivity and tip selection is less critical.

In summary, the invention demonstrates the combination of Raman spectroscopy with a conventional atomic force microscope 12. A fully integrated AFM-Raman instrument is feasible with a relatively simple interface. A significant advantage of Raman spectroscopy is that it is readily directed through fiber optics and the generally weak Raman scattering can be overcome by harnessing the SERS effect. Also the AFM tip 10 can be used as a nanometer scale separation device with the tip subsequently serving as a SERS substrate 16. This allows selective removal of surface layers of interest, in ultra-trace amounts, for identification. This is generically useful in micro-device failure analysis, biological and materials characterization. Raman spectroscopy, with its rich chemical information, now seems poised to be the most readily interfaced spectroscopic technique with an AFM 12. As a potential future application, NASA currently plans to deploy both AFM and Raman instruments on the 2001 Mars Surveyor mission. Later missions, similarly equipped, could exploit AFM targeted SERS for in situ microanalysis of planetary samples.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An apparatus for analyzing a sample comprising:

an atomic force microscope; and a Raman spectrometer optically coupled to the atomic force microscope, wherein the atomic force microscope has a atomic force microscope (AFM) tip with a coating disposed thereon to provide spatially selective enhancement of a Raman signal using a surface enhanced Raman scattering (SERS) effect, where the Raman spectrometer has at least a quasi-monochromatic light source and where the coating is comprised of particles having a size smaller than the shortest wavelength of incident light directed thereon from the light source so that the particles generate surface plasmons, which couple with the sample to produce the enhanced Raman signal, and where the light source illuminates the tip from a side direction approximately perpendicular to an imaginary line connecting the tip and the sample.

2. The apparatus of claim 1 where the coating is sputter-coated gold.

3. The apparatus of claim 1 where the coating is sputter-coated silver.

4. The apparatus of claim 1 where the coating is sputter-coated copper.

5. The apparatus of claim 2 where the sputter-coated gold is Argon sputter coated with a mean grain size of no greater than about 45 nm.

6. The apparatus of claim 1 where the tip is placed directly on a surface of the sample for local surface enhanced Raman spectroscopy.

7. The apparatus of claim 1 where the tip is used to collect surface molecules from the sample and the Raman signal is produced from the collected surface molecules on the tip.

8. The apparatus of claim 1 where the sample comprises a microdevice.

9. The apparatus of claim 1 where the sample comprises an in situ sample.

10. A method for analyzing a sample in an atomic force microscope optically coupled to a Raman spectrometer in which the atomic force microscope has a atomic force microscope (AFM) tip; and a coated tip to enable the generation of a spatially selective enhancement of a Raman signal using a surface enhanced Raman scattering (SERS) effect between the tip and the sample, comprising:

illuminating the sample and tip with at least quasi-monochromatic light in the Raman spectrometer from a side direction approximately perpendicular to an imaginary line connecting the tip and the sample; and generating surface plasmons by using a coating on the tip comprised of particles having a size smaller than the shortest wavelength of incident light from the light source directed onto the tip and sample, to couple the plasmons with the sample to produce a surface enhanced Raman signal.

11. The method of claim 10 further comprising directly placing the tip on a surface of the sample for local surface enhanced Raman spectroscopy.

12. The method of claim 10 further comprising collecting surface molecules from the sample and producing the Raman signal from the collected surface molecules on the tip.

13. The method of claim 10 further comprising sampling a microdevice.

14. The method of claim 10 further comprising sampling an in situ sample.

* * * * *

UNITED STATES PATENT AND TRADEMARK OFFICE
CERTIFICATE OF CORRECTION

PATENT NO. : 6,850,323 B2
DATED : February 1, 2005
INVENTOR(S) : Mark S. Anderson It is certified that error appears in the above-identified patent and that said Letters Patent is hereby corrected as shown below:

Column 1,
Line 3, the following should be inserted
-- The invention described herein was made in the performance of work under a NASA contract, and is subject to the provisions of Public Law 96-517 (35 U.S.C. 202) in which the Contractor has elected to retain title --.

Signed and Sealed this

Ninth Day of August, 2005

JON W. DUDAS
*Director of the United States Patent and Trademark Office*